United States Patent [19]
Yokajty et al.

[11] Patent Number: 6,046,462
[45] Date of Patent: Apr. 4, 2000

[54] METHOD AND APPARATUS FOR DETERMINING ORIENTATION OF PARTS RESTING ON A FLAT SURFACE

[75] Inventors: Joseph E. Yokajty, Webster; Thomas W. Palone, Rochester, both of N.Y.

[73] Assignee: Eastman Kodak Company, Rochester, N.Y.

[21] Appl. No.: 08/991,728

[22] Filed: Dec. 16, 1997

[51] Int. Cl.[7] .................................................. G01N 21/84
[52] U.S. Cl. ............................... 250/559.08; 250/223 R; 250/223 B
[58] Field of Search ......................... 250/559.08, 559.07, 250/223 R, 223 B, 202; 356/239.4, 239.8, 240.1; 198/394

[56] References Cited

U.S. PATENT DOCUMENTS

| | | | |
|---|---|---|---|
| 1,997,712 | 4/1935 | Bauer | 356/379 |
| 3,484,615 | 12/1969 | Noro et al. | 356/379 |
| 3,708,679 | 1/1973 | Stock et al. | 250/223 R |
| 3,778,618 | 12/1973 | Laskowski | 250/223 R |
| 3,837,732 | 9/1974 | Bauer | 359/798 |
| 4,063,823 | 12/1977 | Grat | 356/427 |
| 4,070,575 | 1/1978 | Park et al. | 50/223 R |
| 4,147,433 | 4/1979 | Drinkuth | 356/390 |
| 4,147,930 | 4/1979 | Browne et al. | 250/223 R |
| 4,171,161 | 10/1979 | Jung | 356/383 |
| 4,390,278 | 6/1983 | Inoue | 356/392 |
| 4,459,027 | 7/1984 | Kafri et al. | 356/376 |
| 4,497,576 | 2/1985 | Caussignac et al. | 356/335 |
| 4,509,075 | 4/1985 | Simms et al. | 348/129 |
| 4,678,920 | 7/1987 | Iadipaolo et al. | 250/559.05 |
| 4,786,801 | 11/1988 | Shay | 250/223 B |
| 4,805,124 | 2/1989 | Krufka | 702/155 |
| 4,959,537 | 9/1990 | Kimoto et al. | 250/223 B |
| 5,114,230 | 5/1992 | Pryor | 356/372 |
| 5,280,170 | 1/1994 | Baldwin | 250/225 B |
| 5,314,055 | 5/1994 | Gordon | 198/395 |
| 5,392,360 | 2/1995 | Weindelmayer et al. | 382/151 |
| 5,402,193 | 3/1995 | Choate | 353/80 |
| 5,405,015 | 4/1995 | Bhatia et al. | 209/524 |
| 5,440,385 | 8/1995 | Fein et al. | 356/239.1 |

*Primary Examiner*—Edward P. Westin
*Assistant Examiner*—Thanh X. Luu
*Attorney, Agent, or Firm*—Mark G. Bocchetti

[57] ABSTRACT

An improved lighting system which illuminates the parts with both generally collimated and diffused light simultaneously useful with machine vision systems. This lighting system allows determination of part identification, part location, part orientation about a vertical axis thereof as well as side-up orientation of the part. The parts are transported on a conveyor surface which is made of a translucent medium. However, such translucent medium does permit the viewing of the shadows cast by objects thereon. The light source is positioned directly over the parts being inspected. A camera is positioned below the conveyor surface. Residing between the collimated light source and the parts supported on the conveyor surface is a light-diffusing member. The light-diffusing member has a structure such that it permits a portion of the generally collimated light to pass therethrough without obstruction while simultaneously diffusing a second portion of light produced by the source of collimated light. The combination generally collimated light and diffuse light serve to cast a perimeter shadow of each part and illuminate any downward-facing part surfaces which are not in contact with the conveyor surface. The result is a shadow of different contrasts. Those portions of the parts in contact with the support surface are much darker than those portions of the parts which are elevated away from the support surface.

16 Claims, 3 Drawing Sheets

METHOD AND APPARATUS FOR DETERMINING ORIENTATION OF PARTS RESTING ON A FLAT SURFACE

FIELD OF THE INVENTION

The present invention relates generally to the inspection of three dimensional objects resting on a surface and, more particularly, to the determination of the side-up orientation and location of objects on a surface.

BACKGROUND OF THE INVENTION

Parts feeders used in the manufacturing industry are well known. Typically, such parts feeders comprise bowls or hoppers containing a bulk source of parts. The parts are delivered to a conveying apparatus which is intended to aid in separating the parts. The use of vision-based flexible parts feeders is a relatively new phenomenon in the manufacturing industry which is gaining credibility. With the use of such vision-based parts feeders, companies are able to make their manufacturing systems more flexible in order to cost effectively automate the production of smaller volume products. Typically, in operation, such parts feeders deliver bulk parts from a source to a transport surface for inspection and subsequent picking therefrom by a robot. Preferably, a single camera is used to inspect the separated parts on the transport surface. The inspection is primarily used to identify which parts may be successfully grasped by the robot as well as the location of each identified "pickable" part.

In general, the "flexibility" of a vision-based flexible parts feeder is closely related to the ability of the lighting system to illuminate the widest range of part types in a way that permits successful object recognition by the camera understanding that the different part types are randomly oriented. One flexible parts feeder known in the prior art is the Flexfeeder 250 manufactured by Adept Technologies of San Jose, Calif. This particular feeder comprises a translucent belt on which parts are placed for inspection by a downward-looking camera. Light is projected from the underside of the translucent belt which is more commonly known as backlighting. This lighting method is relatively common and is a very robust means to illuminate a wide variety of parts including parts which have very little color contrast with the belt. However, in many cases where parts possess a profile symmetry, no distinction can be made by the camera as to whether or not the part is right side up or upside down since the image seen by the camera is only its silhouette or perimetric shape. One example of a such a part with perimetric symmetry is a small gear with an axially extending hub on one side. Due to lighting conditions, the backlighting of the Flexfeeder 250 does not permit a distinction to be made between such a gear with the axially extending hub facing upward and such a gear with the axially extending hub facing downward.

Another flexible parts feeder known in the art is the programmable, reconfigurable parts feeder manufactured by Intelligent Automation Systems, Inc., of Cambridge, Mass. This particular parts feeder also utilizes a translucent belt on which parts are placed in single file for inspection by a downward-looking camera. In addition, a mirror is located next to the part inspection location and tilted at 45 degrees. This allows a "second view" without the need for adding another camera. Depending on the specific part geometry, this may or may not provide the information needed to determine actual part orientation because the shape of the "second view" of the part may vary with orientation of the part about its vertical axis.

U.S. Pat. No. 5,280,170 to Baldwin teaches an inspection machine wherein a vertically standing container is transported to an inspection location on a transparent conveyor. There is a diffuser plate located beneath the transparent container. A beam of collimated light is directed vertically downward toward the diffuser plate and a two-dimensional camera actually views the shadow of the container cast onto the diffuser plate and the image is processed to evaluate circumference of the container. Thus, Baldwin's machine has the capability of only viewing the silhouette. Side-up orientation of the vertically standing container is known prior to inspection.

The prior art fails to teach a method or apparatus wherein parts (there may be several different types of parts present) can be visually inspected by a single camera such that randomly oriented parts can be identified and further, the side-up orientation of such parts can be determined.

SUMMARY OF THE INVENTION

It is, therefore, an object of the present invention to provide a method and apparatus which can reliably inspect three dimensional objects resting on a surface such that part type, part location, side-up orientation and orientation about a vertical axis can be determined with a single camera.

Another object of the present invention is to provide a method and apparatus for illuminating three dimensional objects supported on a surface in a way which enables inspection with a single CCD camera or with other image capturing means.

Briefly stated, the foregoing and numerous other features, objects and advantages of the present invention will become readily apparent upon a reading of the detailed description, claims and drawings provided herein. These features, objects and advantages are accomplished with the use of an improved lighting system which illuminates the parts with both generally collimated and diffused light simultaneously. This lighting system allows determination not only of part silhouette information but also determination of those portions of the parts which are in contact with the conveyor surface. The parts are transported on a conveyor surface which is made of a translucent medium, that is a medium which transmits rays of light so diffused that objects cannot be seen distinctly therethrough. However, such translucent medium does permit the viewing of the shadow cast by objects thereon. The light source is positioned directly over the parts being inspected. A camera is positioned below the conveyor surface. Residing between the collimated light source and the parts supported on the conveyor surface is a light-diffusing member. The light-diffusing member has a structure such that it permits a portion of the generally collimated light to pass therethrough without obstruction while simultaneously diffusing a second portion of light produced by the source of collimated light. The first portion of light which remains generally collimated casts a perimeter shadow of each part or object supported on the conveyor surface and the camera is able to see that shadow and determine part type by its silhouette or perimetric shape. The second portion of light which is uniformly diffused tends to scatter and reflect off the top surface of the conveyor thereby illuminating the downward-facing object or part surfaces which are not in contact with the conveyor surface. The result is a shadow of different contrasts. Those portions of the parts in contact with the support surface are much darker than those portions of the parts which are elevated away from the support surface. In such manner, the image received by the camera can be used to distinguish not only part type, part location and part orientation about a vertical axis, but also side-up orientation of the part.

DETAILED DESCRIPTION OF THE INVENTION

Figure 1:
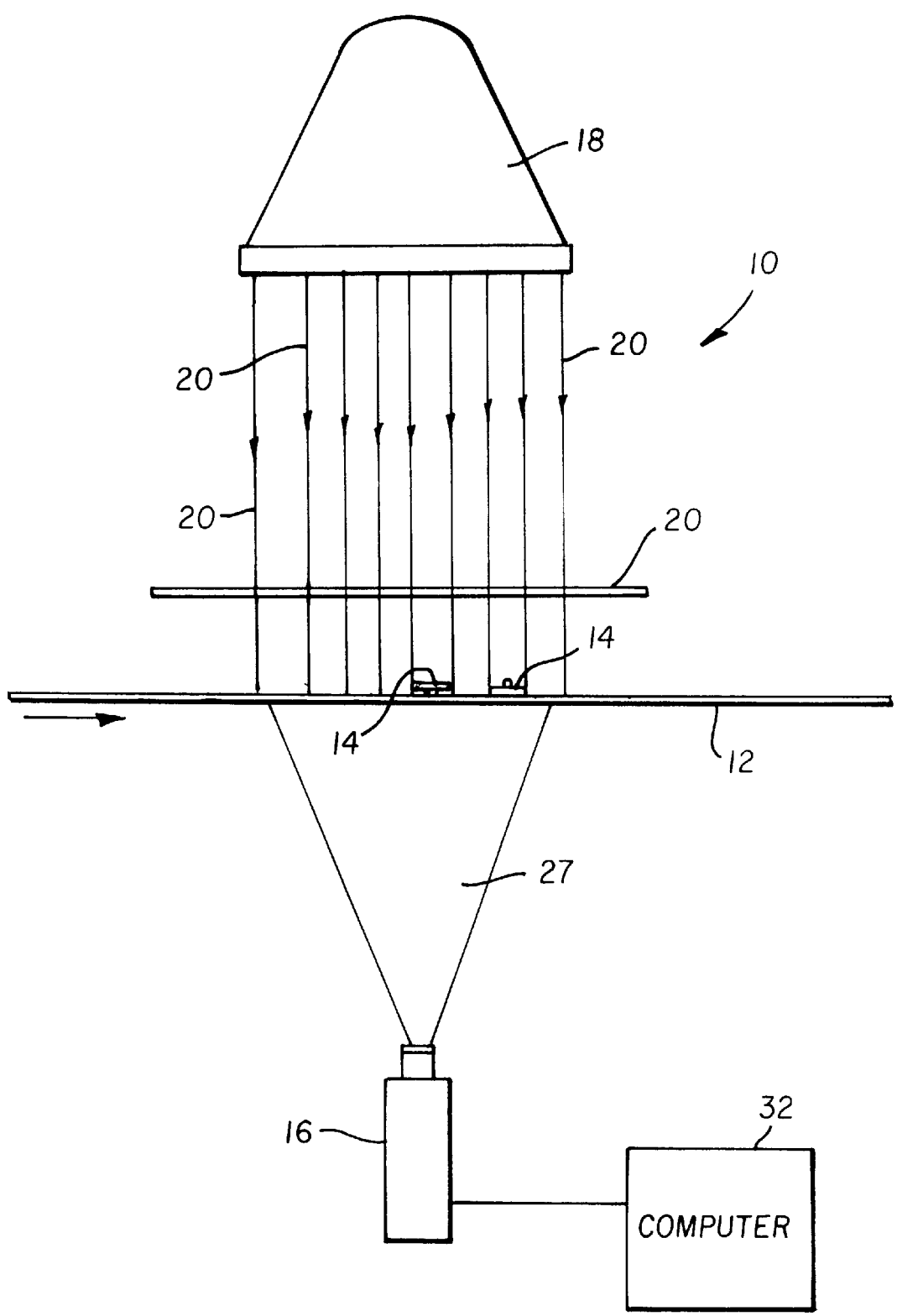
FIG. 1 is a schematic side elevation of the apparatus of the present invention.
Figure 2:
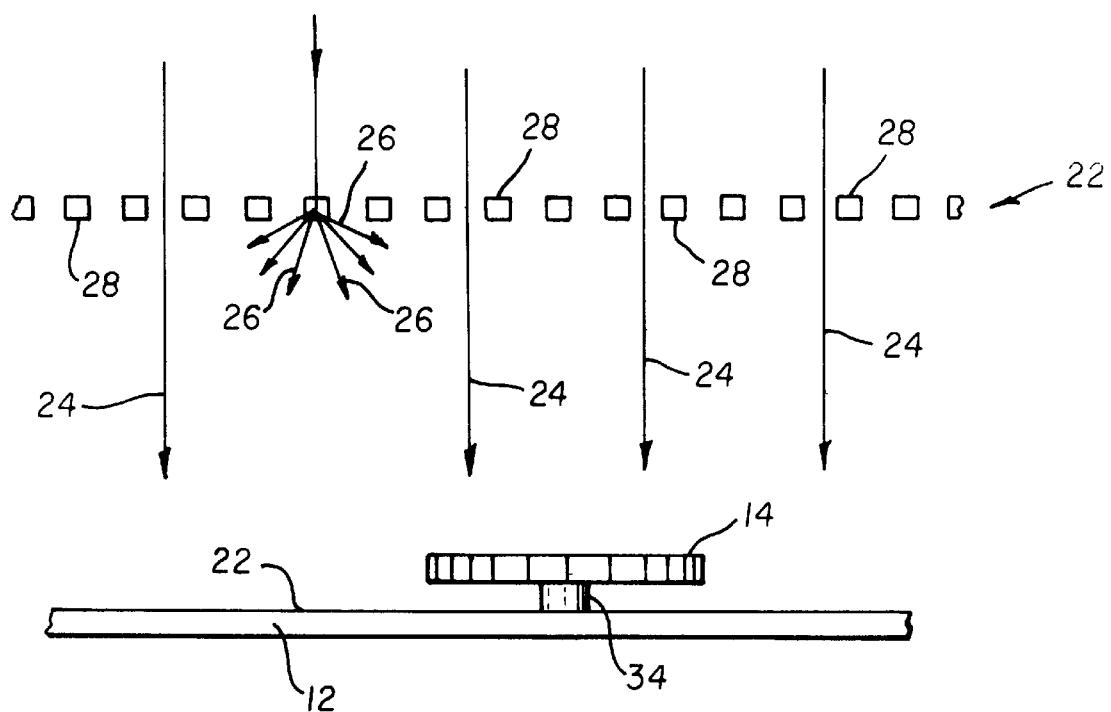
FIG. 2 is the image seen by a camera of two identical parts supported on the support member with opposite side-up orientations.

Turning first to FIG. 1, there is schematically depicted the apparatus 10 of the present invention. The apparatus 10 includes a support member 12 upon which objects or parts 14 are conveyed. Thus, support member 12 is preferably part of a conveyor belt apparatus driven and supported by means not shown. Support member 12 may also be part of a different type conveying apparatus such as such as slip-stick conveyor or a vibratory conveyor. Positioned beneath support member 12 is an image capture means 16. Image capture means 16 is a camera device such as a CCD image sensor array, a CMOS image sensor array, or a photo diode array. In addition, image capture means 16 may use vidicon tube technology. Positioned above support member 12 is a collimated light source 18 which emits generally collimated light vertically downward toward support member 12 and parts 14. Collimated light source 18 may include a structure which can be used to collimate light such as a Fresnel lens. Collimated light source 18 may also be a point light source. Thus, the term "generally collimated light" as used herein is intended to include light from a collimated light source and light from a point light source. The term "collimated light source" as used herein is intended to include a collimated light source and a point light source. Located between collimated light source 18 and support member 12 is a light diffusing member 22 supported by means not shown. Light diffusing member 22 is preferably supported in close proximity to parts 14 and is positioned directly over that section of support member 12 where parts 14 are to be inspected. The area of light diffusing member 22 should preferably be greater than the area of the field of view 27 of camera 16 at support member 12. Light diffusing member 22 must possess two specific optical characteristics. It must first permit a certain portion of the generally collimated light 20 emitted from collimated light source 18 to pass therethrough without obstruction as indicated by arrows 24 as depicted in FIG. 2. Light diffusing member 22 must also be able to diffuse a second portion of generally collimated light 20 emitted from collimated light source 18 as indicated by arrows 26. For this reason, light diffusing member 22 comprises tiny optical features 28 which diffuse that second portion of generally collimated light. Optical features 28 should be small enough in diameter or size such that optical features 28 and any shadows cast by optical features 28 cannot be detected by camera 16. Optical features 28 having a diameter of about 5 mils are more than adequate for this purpose. The diameter of optical features 28 may range as high as 10 mils or more depending on the type and specification of the particular camera 16 being used. In addition, a blur filter could be used to disable the ability of camera 16 to detect optical features 28 and any shadows cast by optical features 28. Light diffusing member 22 may be made from a variety of materials and have a variety of structures. For example, light diffusing member 22 may be a thin clear web with an optical micro-replication pattern on its top surface. The clear portions of the web would allow the generally collimated light incident therewith to pass therethrough substantially unaffected. The optical micro-replication pattern would diffuse that portion of the generally collimated light that is incident therewith. Light diffusing member 22 may take the form of glass or plastic with selective laser marking of the surface thereof to create the desired light diffusing property. Alternatively, light diffusing member 22 may be a piece of clear glass or plastic with a finely etched pattern on the top surface. Similarly, light diffusing member 22 may be a clear plastic film a fine pitch pattern printed thereon with a translucent ink, or a clear plastic film which is partially textured to achieve the desired light diffusing characteristic. The preferred material for light diffusing member 22 is a piece of fine mesh silk-screen. The openings through the silk-screen would permit the generally collimated light to pass therethrough. The threads would diffuse that portion of the generally collimated light which is incident therewith. A silk-screen with threads having a diameter of about three (3) mils and a pattern pitch of seven (7) mils was used successfully in testing the present invention. The area of this particular silk-screen was made up of about 33 percent openings and 67 percent threads. Thus, that portion of generally collimated light 14 which passes directly through this particular silk-screen should also be about 33 percent. It is believed that a wide range of silk-screens could be used in the practice of the present invention. Ranges for fiber diameter and pattern pitch can be determined empirically for any particular apparatus 10 and the objects 14 to be inspected thereby. Light diffusing member 22 should function adequately by diffusing a portion in the range of from about from about 40 percent to about 80 percent of the generally collimated light. The range of that portion of the generally collimated light which may be diffused by light diffusing member 22 may be even greater depending on the particular apparatus 10 and the objects 14 to be inspected thereby. Certainly such range can be determined empirically for any particular implementation of the present invention.

Support member 12, on the other hand, is preferably made from a thin translucent material which does not permit direct viewing of the objects 14 supported thereon by the camera 16. As used herein, the term "translucent" is intended to mean transmitting and diffusing light so that objects beyond cannot be seen clearly. However, the translucent quality of support member 12 permits the viewing of shadows cast by objects 14 onto support member 12. In other words, although camera 16 cannot view objects 14 clearly and/or directly through support member 12, camera 16 can view the shadow of objects 14 cast onto the top surface 30 of support member 12. In addition, the top surface 30 of support member 12 must be able to effectively reflect a portion of the diffused light 26 falling on top surface 30. Thus, the second portion of light (the diffused light 26) falling on top surface 30 tends to uniformly scatter, reflect off the top surface 30 of support member 12 and then illuminate the downward-facing surfaces of object 14 which are not in contact with the top surface 30 of support member 12. The preferred material for support member 12 is a white, translucent plastic film. One example of a suitable material for use as support member 12 is a 4 mil double matte polyester film JET SET™ JR 440 IJM as sold by Rexham Graphics of South Hadley, Mass. Another material which can be used for support member 12 is a 4 mil polyester film produced by ICI called Melinex™. A variety of other materials may also be used such as, for example, translucent paper drafting film.

Figure 3:
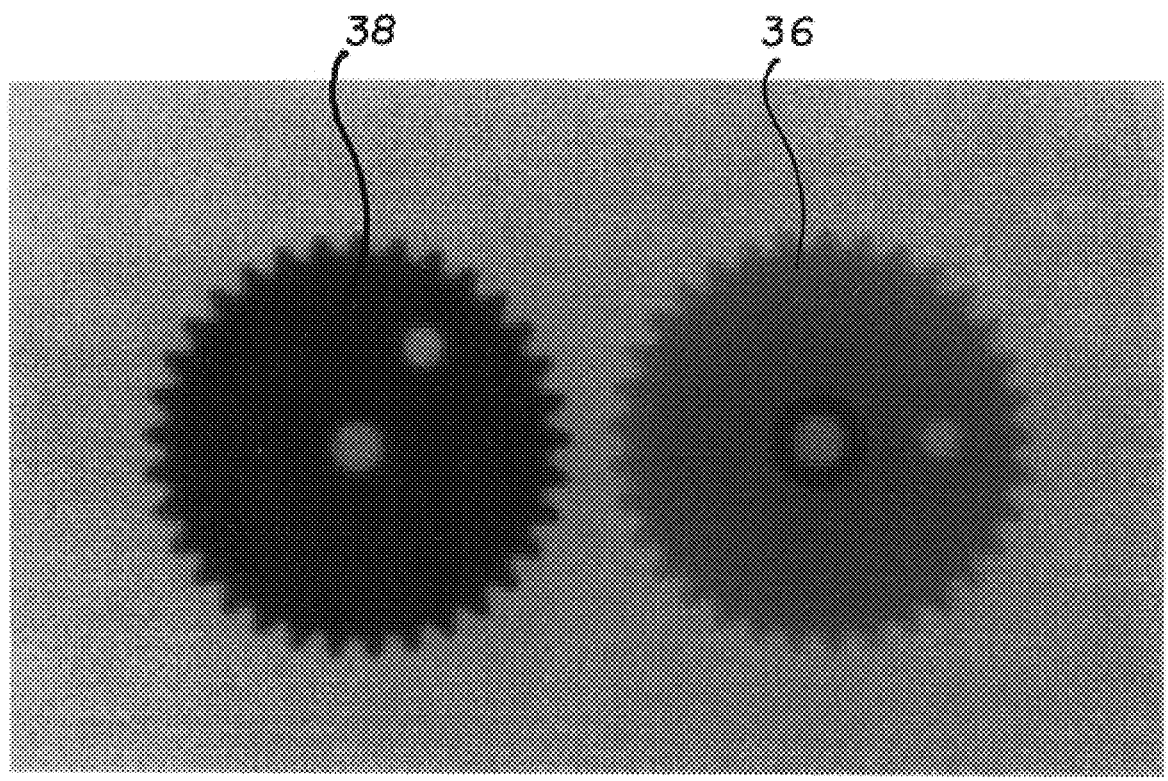
FIG. 3 is a schematic of a side elevational view of generally collimated light passing through the light diffusing member and illuminating an object supported on the support member.

The image seen by camera 16 is evaluated by a computer 32 which is programmed with comparative images of the part 14 being conveyed on support member 12. The resulting images seen by camera 16 allows the computer 32 to make a distinction between upside down and right side up parts 14. For example, assuming that part 14 as depicted in FIG. 2 is a gear with an axially extending hub portion 34 on one side thereof, camera 16 would view an image or shadow 36 (See FIG. 2) as depicted in FIG. 3 when the hub 34 is supported on surface 30 and would view an image or shadow 38 when the gear side of part 14 is in contact with surface 30 of support member 12. Note the difference in contrast. With the gear side in contact with top surface 30, a sharply contrasted shadow 38 is produced of a single dark shade. When the hub 34 is supported on surface 30 of support member 12, a different shadow 36 is produced. The perimetric shadow or silhouette of the gear remains the same as that of shadow 38. However, the hub portion of that shadow is darker than the gear portion for reason that the hub portion is actually in contact with surface 30. The diffused light 26 which has reflected off of surface 30 has illuminated the downward facing surface of the part 14 which is elevated above surface 30. By illuminating such downward surface, the shadow cast by that part of the object 14 is not as dark. Thus, by use of the method and apparatus of the present invention, the computer 32 can readily distinguish the type of object supported on support member 12 by means of its perimetric shadow or silhouette and can further distinguish its side-up orientation.

It should be understood that due to camera resolution limitations and/or the slightly diffused quality of the generally collimated light 20 emitted from collimated light source 18, any shadows cast by features 28 cannot be detected by camera 16.

Alternatively, light diffusing member 22 may be replaced with a type of liquid crystal display panel sold as a "privacy electronic film panel" manufactured by 3M's Privacy Film Division. This panel may be turned from a translucent state by applying a specified voltage to the device. However, use of such a panel would require that two inspections be made of each object 14 to be inspected. With the specified voltage applied and the panel clear, the first inspection would make an evaluation based on a well defined cast silhouette of each object 14. The first inspection would be made with a first portion (in time) of collimated light. With the specified voltage turned off and the panel translucent, the second inspection is made based upon the darker areas which are in contact with the support surface 30 and, thus, not partially illuminated by the diffused light 26 reflecting off of surface 30. The second inspection would be made with a second portion (in time relative to the first portion) of the collimated light, much of which is diffusely reflected by the privacy electronic film panel.

The lighting of the present invention results in the ability to reliably "see" different images that are not only a function of the inspected object's shape but also the shape of the contact area between the object 14 and the support member 12. The image of the object 14 for a particular side-up orientation is not affected by the object's location within the camera field of view due to the uniformity of the lighting across the entire field of view. As such, this lighting method may be used to achieve a universal lighting technique for use with vision-based flexible parts feeders.

From the foregoing, it will be seen that this invention is one well adapted to attain all of the ends and objects hereinabove set forth together with other advantages which are apparent and which are inherent to the invention.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth and shown in the accompanying drawings is to be interpreted as illustrative and not in a limiting sense.

What is claimed is:

1. An apparatus for determining an object's type and side-up orientation comprising:

(a) a translucent support member having a top surface on which the object is supported;

(b) means for emitting a generally collimated light vertically downward to illuminate said top surface;

(c) means positioned between said translucent support member and said means for emitting for diffusing a first portion of said generally collimated light while allowing a second portion of said generally collimated light to pass therethrough unaffected, said top surface reflecting an amount of any of said first portion which is incident thereon; and (d) an imaging capturing means located below said translucent support member, said imaging capturing means viewing the object as a result of said first portion and said second portion.

2. An apparatus for determining an object's type and side-up orientation comprising:

(a) a translucent support member having a top surface on which the object is supported;

(b) a source of light positioned above said translucent support member, said source of light directing a generally collimated light vertically downwardly toward said translucent support member;

(c) a light diffusing member positioned between said translucent support member and said source of light, said light diffusing member diffusing a portion of said generally collimated light to yield a diffuse light with a remainder of said generally collimated light remaining generally collimated, said top surface reflecting an amount of any of said diffuse light which is incident thereon; and (d) an image capturing means located below said translucent support member, said image capturing means viewing a shadow cast by the object as a result of said first portion and said second portion.

3. An apparatus as recited in claim 2 further comprising: a computer for evaluating the shadow.

4. An apparatus as recited in claim 2 wherein: said support member is a white translucent plastic film.

5. An apparatus as recited in claim 2 wherein: said light diffusing member is a fine mesh silk-screen.

6. An apparatus as recited in claim 2 wherein: said image capturing means is a CCD camera.

7. An apparatus as recited in claim 2 wherein: said light diffusing member is a clear plastic film with a fine, light diffusing pattern imparted thereto.

8. An apparatus as recited in claim 2 wherein: said light diffusing member is a clear glass with a fine, light diffusing pattern imparted thereto.

9. An apparatus as recited in claim 2 wherein:
said image capturing means is a CMOS image sensor array.

10. An apparatus as recited in claim 2 wherein:
said image capturing means is a camera.

11. An apparatus as recited in claim 2 wherein:
said image capturing means is a photo diode array.

12. An apparatus as recited in claim 2 wherein:
said image capturing means is vidicon camera.

13. A method for determining an object's type and side-up orientation comprising the steps of:

(a) supporting the object on a translucent support member;

(b) directing a generally collimated light vertically downwardly toward said translucent support member;

(c) diffusing a portion of the generally collimated light to yield a diffuse light;

(d) reflecting at least some of the diffuse light to illuminate any downwardly facing surfaces of the object which are not in contact with the support member; and (e) capturing an image of a shadow cast by the object on the support member.

14. A method as recited in claim 13 further comprising the step of:
evaluating the image.

15. A method as recited in claim 13 further comprising the step of:
comparing the image to a series pre-programmed images of possible objects and orientations to determine object type and object orientation.

16. A lighting method for illuminating objects for use with machine vision comprising:

(a) directing generally collimated light vertically downward at a horizontal support member, the object to be illuminated resting on the horizontal support member;

(b) diffusely reflecting a portion of the generally collimated light with the support member; and (c) passing a remainder of the generally collimated light directly through the support member.

* * * * *